United States Patent

Flick et al.

[11] Patent Number: 5,847,250
[45] Date of Patent: Dec. 8, 1998

[54] SUPPORTED PALLADIUM CATALYST FOR SELECTIVE CATALYTIC HYDROGENATION OF ACETYLENE IN HYDROCARBONACEOUS STREAMS

[75] Inventors: Klemens Flick, Herxheim; Christof Herion, Ladenburg; Hans-Martin Allmann, Neunkirchen, all of Germany

[73] Assignee: BASF Aktiengesellschaft, Ludwigshafen, Germany

[21] Appl. No.: 984,844

[22] Filed: Dec. 4, 1997

Related U.S. Application Data

[62] Division of Ser. No. 711,904, Sep. 12, 1996.

[30] Foreign Application Priority Data

Sep. 23, 1995 [DE] Germany .................. 195 35 402.8

[51] Int. Cl.$^6$ .............................. C07C 5/08; C07C 7/167
[52] U.S. Cl. ......................... 585/260; 585/259; 585/261; 585/273; 585/275; 585/277
[58] Field of Search ..................... 585/259, 260, 585/261, 273, 275, 277, 258; 208/143, 144

[56] References Cited

U.S. PATENT DOCUMENTS 5,057,206 10/1991 Engel et al. ............................. 208/143
5,489,565 2/1996 Cheung et al. ......................... 502/325

*Primary Examiner*—Bekir L. Yildirim
*Attorney, Agent, or Firm*—Keil & Weinkauf

[57] ABSTRACT

A silica-supported catalyst suitable for the selective hydrogenation of acetylene in hydrocarbonaceous streams, comprising from 0.001 to 1% by weight, based on the supported catalyst, of palladium and from 0.005 to 5% by weight, based on the supported catalyst, of at least one promoter metal of groups 1 and 2 of the periodic table, obtainable by impregnating a silica support with a solution comprising at least one promoter metal, drying the impregnated support, impregnating with a palladium-including solution, drying and calcining.

2 Claims, No Drawings

SUPPORTED PALLADIUM CATALYST FOR SELECTIVE CATALYTIC HYDROGENATION OF ACETYLENE IN HYDROCARBONACEOUS STREAMS

This application is a division of Ser. No. 08/711,904, filed on Sep. 12, 1996.

The present invention relates to novel silica-supported catalysts suitable for the selective catalytic hydrogenation of acetylene in hydrocarbonaceous streams.

This invention further relates to a process for preparing these catalysts, and to a process for the selective hydrogenation of acetylene in hydrocarbonaceous streams using the catalysts of this invention.

Acetylene is an undesirable constituent of feedstocks for various industrial reactions because it tends to polymerize and to inactivate transition metal catalysts. More particularly, acetylene is technically disadvantageous in the $C_2$ streams from steam crackers. These streams are essentially ethylene and ethane together with small amounts of acetylene. The acetylene content has to be reduced to less than 1 ppm for these streams to be used for producing polyethylene. Catalysts suitable for a hydrogenation of acetylene have to meet high requirements in terms of their selectivity and activity, since the hydrogenation is to take place without loss of ethylene.

The catalysts used for this purpose are predominantly alumina-supported palladium catalysts. Prior proposals include catalysts comprising palladium on macroporous $Al_2O_3$ supports having a BET surface area of from 0.1 to 2 $m^2/g$ (JP-B 80/047 015; Chem. Abstr., Vol. 82, 169991), which comprise palladium and optionally chromium on supports having a surface area of less than 5 $m^2/g$ (U.S. Pat. No. 4,577,047), or which, as well as palladium, include silver (EP-A 64 301), gold (EP-A 89 252), lithium (U.S. Pat. No. 3,325,556), chromium (DE-A 12 84 403) or potassium as promoters (Park et al., J. Chem. Soc., Chem. Commun. 1991, 1188; Ind. Eng. Chem Res. 31 (1992) 469).

U.S. Pat. No. 4,839,329 describes $TiO_2$ as a further support material for palladium catalysts for the selective hydrogenation of acetylene. U.S. Pat. No. 4,906,800 teaches palladium-lead catalysts based on $CaCO_3$. DE-A 21 56 544 relates to palladium-zinc catalysts on silica.

German Patent Application P 19 500 366.7 relates to supported palladium catalysts prepared by impregnating a support with a palladium sol.

The hydrogenation of small amounts of acetylene in hydrocarbonaceous streams using the catalysts mentioned requires the addition of carbon monoxide to the stream to be hydrogenated in order that the selectivity of the respective catalyst may be enhanced. This has the disadvantage that the selectivity-increasing effect of the carbon monoxide is strongly temperature-dependent. Large temperature gradients in the catalyst bed therefore have an adverse effect on the selectivity. In addition, the metered addition of relatively small amounts of carbon monoxide to comparatively large streams requires a considerable measurement and control effort.

Furthermore, the catalysts mentioned include in part large amounts of costly noble metals, which make their use on a large industrial scale economically prohibitive.

It is an object of the present invention to provide catalysts which do not have these disadvantages. More particularly, they shall be capable of hydrogenating even small amounts of acetylene in hydrocarbonaceous streams with high selectivity without addition of carbon monoxide.

We have found that this object is achieved by silica-supported catalysts comprising from 0.001 to 1% by weight, based on the supported catalyst, of palladium and from 0.005 to 5% by weight, based on the supported catalyst, of at least one promoter metal of groups 1 and 2 of the periodic table, obtainable by impregnating a silica support with a solution comprising at least one promoter metal, drying the impregnated support, impregnating with a palladium-including solution, drying and calcining.

The present invention also provides a process for preparing the catalysts of this invention, and also a process for hydrogenating acetylene using said catalysts The supported catalysts of this invention are prepared by stepwise impregnation of a silica support. These supports can be used in any desired form, for example, as granules, pellets or tablets, but preferably as extrudates. It is advantageous to use silica having a BET surface area of not less than 50 $m^2/g$, and preference is given to supports having a surface area of from 100 to 300 $m^2/g$. The chemical history of the silica used has no discernible bearing on the performance of the catalysts of this invention; precipitated or pyrogenic silica can be used, for example.

The first impregnation applies the promoter to the support. Advantageously, this is done by admixing the support with the maximum amount of solution it can absorb. This solution will contain such an amount of promoter metal that the finally calcined catalyst will contain an amount of from 0.005 to 5% by weight of promoter metal. Suitable mixing ratios are readily determinable by those skilled in the art on the basis of a few preliminary experiments.

Suitable promoter metals include alkali and alkaline earth metals such as lithium, sodium, potassium, rubidium, cesium, calcium, strontium and barium. Of these, preference is given to rubudium, strontium and barium, and very particular preference is given to potassium. It is possible to apply not just one but more than one of the promoter metals mentioned. The promoter metals are customarily dissolved in solvents, preferably water, in the form of their salts. Suitable salts include in particular those salts which are readily calcinable into the corresponding oxides, for example hydroxides, carbonates, nitrates, acetates and formates of the promoter metals mentioned, of which the hydroxides are preferred.

After impregnation with the promoter metal(s), the support is dried. The drying generally takes place at temperatures below 300° C., since the prolonged action of high temperatures will increasingly favor the formation of silicates. The drying generally takes from 5 to 20 h. It is complete when the evolution of solvent has stopped.

The second impregnation applies palladium to the pretreated support in a conventional manner. As in the case of the promoter metal(s), this is preferably done by impregnation with a solvent quantity which the support can absorb completely. The support is admixed with a palladium salt solution. Water is the preferred solvent for the palladium salt. Only genuine solutions are used; that is, palladium-including sols are not used. Suitable palladium salts include for example palladium nitrate, palladium acetate, palladium acetylacetonate and palladium chloride. Some of these palladium salt solutions are acidic because of the anions used.

In a preferred embodiment, neutral solutions are rendered acidic, for example with mineral acids, before the impregnation.

After the support has been impregnated with the palladium salt solution, it is dried. The drying temperature is in general from 100° to 200° C. over a period of from 5 to 20 h. In the course of the drying, the support is preferably agitated in order that uniform drying may be achieved.

Subsequently the dried supports are calcined, generally at temperatures of from 300° to 700° C., preferably of from 320° to 450° C., over a period of from 0.5 to 8 h.

Before employing the catalysts of this invention in a process for the hydrogenation of acetylene, they can be activated by reduction with hydrogen or a hydrogen-including gas at temperatures which generally extend from 100° to 550° C., in which case the hydrogen partial pressure is advantageously from 1 to 300 bar and the reduction is carried on until the formation of water has ceased.

The catalysts of this invention have a thin layer of palladium on a promoter metal oxide. This catalyst construction results in high selectivity.

The catalysts of this invention may, for example, be employed for the selective hydrogenation of acetylene in hydrocarbonaceous streams. Of special interest in this connection are steam cracker streams which include acetylene in amounts of from 0.01 to 5% by volume as well as ethylene and ethane as main constituents.

Acetylene-including hydrocarbonaceous streams are hydrogenated in the gas phase at hydrogen pressures ranging in general from 10 to 30 bar. Depending on the amount of acetylene to be hydrogenated, the hydrogenation can be carried out in one or more stages and with or without intermediate cooling and hydrogen feeds into each individual reactor in a conventional manner. An adiabatic process is preferred and is readily achieved for acetylene contents of below 1% by volume. The inlet temperature of the acetylene-including hydrocarbonaceous streams into the first reactor is generally from 15° to 120° C., preferably from 25° to 95° C. When only one reactor is used, the molar ratio of hydrogen to acetylene is generally from 1.1:1 to 2:1, preferably from 1.2:1 to 1.6:1. With a plurality of consecutive reactors with hydrogen feed into each reactor, by contrast, it can be within the range from 0.6:1 to 1.2:1.

The catalysts of this invention are very active in the hydrogenation of acetylene and can be used at relatively low temperatures. They are highly selective even at low acetylene contents without carbon monoxide having to be metered into the hydrogenation stage. It is possible to achieve residual acetylene contents of about 1 ppm, and, compared with existing catalysts, low stoichiometric hydrogen excesses can be used.

EXAMPLES

Example 1
Preparation of a potassium-doped catatlyst 111 kg of a silica gel support (diameter 4 mm) having a BET surface area of 270 m$^2$/g were impregnated with 92 l of a solution of 330 g of potassium hydroxide in water. The support was dried by agitating it at 120° C. for 16 h. The second impregnation was carried out with 95 l of an aqueous solution of palladium nitrate having a palladium content of 33 g. After drying at 120° C. over a period of 16 h, the extrudates were calcined at 400° C. over 4 h.

Example 2
Selective hydrogenation of acetylene using a catalyst of this invention A tubular reactor having a diameter of 305 mm was charged with 50 l of Example 1 catalyst. The reactor was flushed with nitrogen. The catalyst was then reduced with 20 bar of hydrogen at 150° C. over 3 h.

The reactor was charged with 150 m$^3$/h of a stream including 0.71% by volume of acetylene as well as 69.6% by volume of ethylene and 29.6% by volume of ethane and also with hydrogen having an inlet temperature of 35° C. The molar ratio of hydrogen to acetylene was reduced step by step. Table 1 shows the reaction details.

TABLE 1

| mol of H$_2$/mol of acetylene | Acetylene content after hydrogenation (ppm) | Conversion (%) | Selectivity (%) |
|---|---|---|---|
| 1.81 | <0.1 | >99.999 | 19 |
| 1.54 | <0.1 | >99.999 | 46 |
| 1.43 | <0.1 | >99.999 | 56 |

We claim:

1. A process for the selective catalytic hydrogenation of acetylene with hydrogen in hydrocarbonaceous streams, which comprises hydrogenating the acetylene in the gas phase over a catalyst consisting essentially of from 0.001 to 1% by weight, based on the supported catalyst, of palladium and from 0.005 to 5% by weight, based on the supported catalyst, of at least one promoter metal of groups 1 and 2 of the periodic table, said catalyst being obtained by impregnating a silica support with a solution comprising at least one of said promoter metals, drying the impregnated support, impregnating with a palladium-including solution, drying and calcining.

2. A process as defined in claim 1, wherein acetylene is selectively hydrogenated in an essentially ethylene- and ethane-comprising stream that includes from 0.01 to 5% by volume of acetylene.

* * * * *